United States Patent
Simon et al.

(10) Patent No.: US 6,632,246 B1
(45) Date of Patent: Oct. 14, 2003

(54) CARTILAGE REPAIR PLUG

(75) Inventors: Timothy M. Simon, Los Alamitos, CA (US); Harold M. Aberman, Montclair, NJ (US); Douglas W. Jackson, Long Beach, CA (US)

(73) Assignee: ChondroSite, LLC, Irvine, CA (US)

( * ) Notice: Subject to any disclaimer, the term of this patent is extended or adjusted under 35 U.S.C. 154(b) by 0 days.

(21) Appl. No.: 09/525,437

(22) Filed: Mar. 14, 2000

(51) Int. Cl.[7] .............................. A61F 2/08; A61F 2/36
(52) U.S. Cl. ................. 623/14.12; 623/23.48
(58) Field of Search ................ 623/23.47, 23.72, 623/17.17, 17.16, 23.48, 23.51, 23.39, 23.56, 23.61, 23.62, 14.12

(56) References Cited

U.S. PATENT DOCUMENTS

| | | |
|---|---|---|
| 3,875,595 A | 4/1975 | Froning |
| 4,222,128 A * | 9/1980 | Tomonaga et al. ............. 106/35 |
| 4,446,578 A | 5/1984 | Perkins et al. |
| 4,570,270 A | 2/1986 | Oechsle, III |
| 4,641,651 A | 2/1987 | Card |
| 4,743,632 A | 5/1988 | Marinovic |
| 4,904,260 A | 2/1990 | Ray et al. |
| 4,938,763 A | 7/1990 | Dunn et al. |
| 4,955,911 A * | 9/1990 | Frey et al. ................ 623/23.51 |
| 5,007,940 A | 4/1991 | Berg |
| 5,067,964 A * | 11/1991 | Richmond et al. ........ 623/14.12 |
| 5,077,049 A | 12/1991 | Dunn et al. |
| 5,130,347 A | 7/1992 | Mitra |
| 5,278,201 A | 1/1994 | Dunn et al. |
| 5,324,519 A | 6/1994 | Dunn et al. |
| 5,340,849 A | 8/1994 | Dunn et al. |
| 5,414,049 A | 5/1995 | Sun et al. |
| 5,458,643 A * | 10/1995 | Oka et al. ................. 623/17.16 |
| 5,468,787 A | 11/1995 | Braden et al. |
| 5,556,429 A | 9/1996 | Felt |
| 5,599,552 A | 2/1997 | Dunn et al. |
| 5,607,474 A | 3/1997 | Athanasiou et al. |
| 5,655,546 A | 8/1997 | Halpern |
| 5,723,331 A | 3/1998 | Tubo et al. |
| 5,750,651 A | 5/1998 | Opermann et al. |
| 5,769,899 A * | 6/1998 | Schwartz et al. ............. 606/77 |
| 6,149,688 A * | 11/2000 | Brosnahan et al. ......... 623/23.5 |

FOREIGN PATENT DOCUMENTS

| | | |
|---|---|---|
| FR | 2636823 | 6/1990 |
| WO | WO 97/13533 | 6/1990 |
| WO | WO 96/39169 | 12/1996 |
| WO | WO 96/39170 | 12/1996 |

OTHER PUBLICATIONS

Doctor's Guide, "New Technique To Repair Common Sports injury Fields Excellent Results", http://www.psl-group.com/dg/462a2.htm.*

* cited by examiner

Primary Examiner—Corrine McDermott
Assistant Examiner—Hieu Phan
(74) Attorney, Agent, or Firm—Fulwider Patton Lee & Utecht, L.L.P.

(57) ABSTRACT

A cartilage plug, which is made from a biocompatible, artificial material, that is used to fill a void in natural cartilage that has been resected due to traumatic injury or chronic disease is disclosed. Alternatively, the plug may be relied upon to anchor a flowable polymer to subchondral bone. The plug is prebricatable in any size, shape, and contour and may be utilized either singly or in a plurality to fill any size void for any application. The plug may be formed of a laminated structure to match the physiological requirements of the repair site. Additionally, ridges may be formed about the periphery of each plug to facilitate its anchoring to surrounding cartilage, bone and/or adjacent plugs. A procedure for resecting damaged or diseased cartilage and for implanting a replacement plug or plugs according to this invention, as well as a set of instruments for effecting the procedure, and a self-contained system for orthopedic surgeons, which includes a variety of differently sized and shaped plugs, as well as a set of instruments for the procedure are also disclosed.

1 Claim, 8 Drawing Sheets

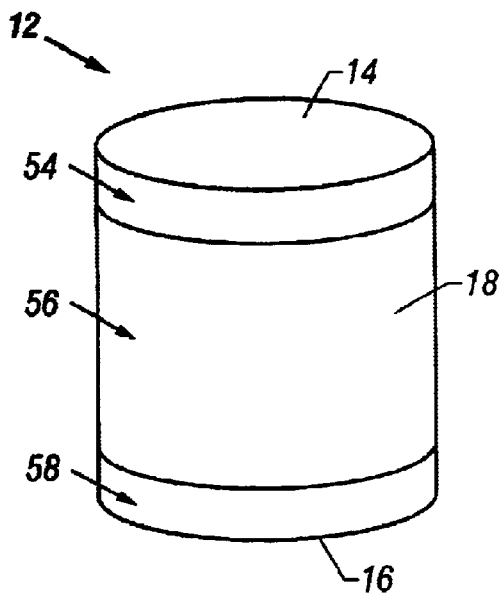
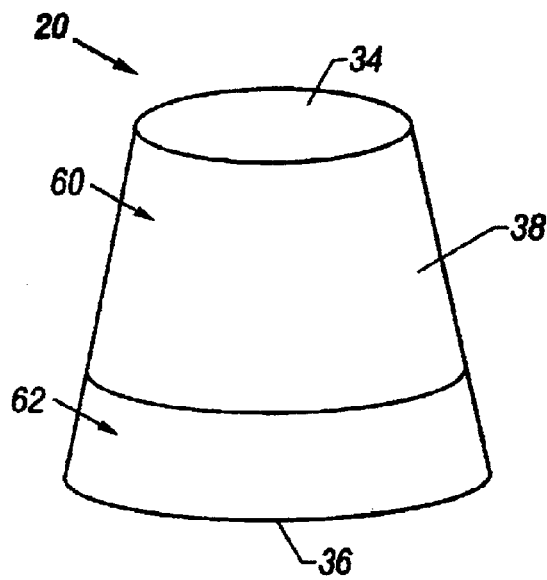
FIG. 1
FIG. 2
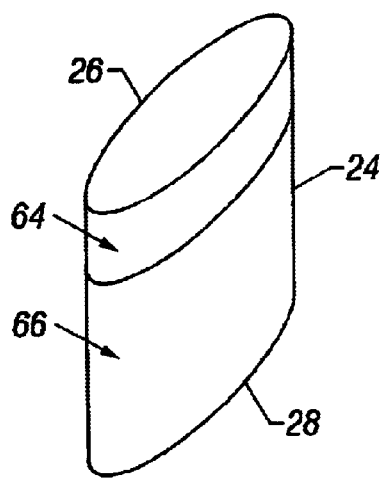
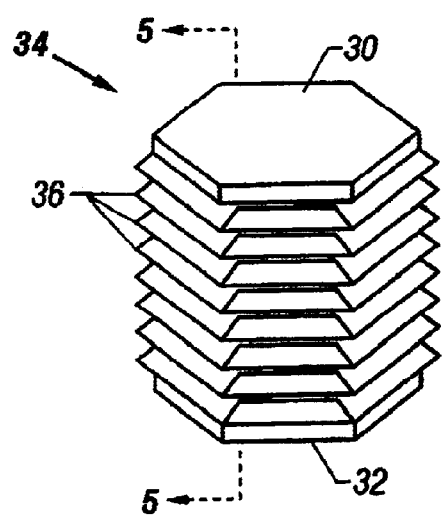
FIG. 3
FIG. 4

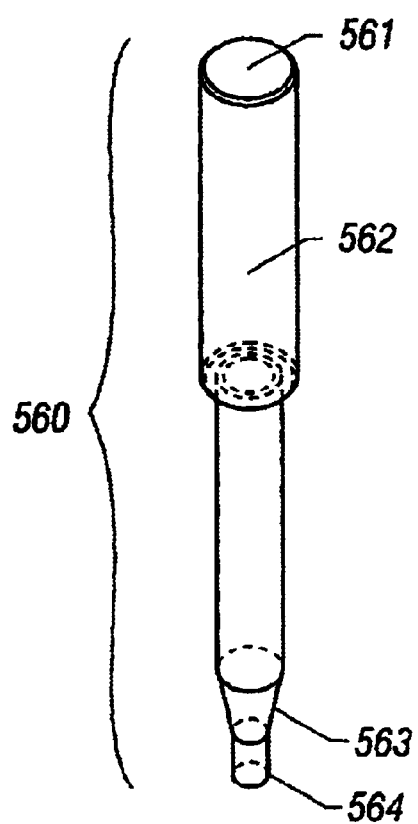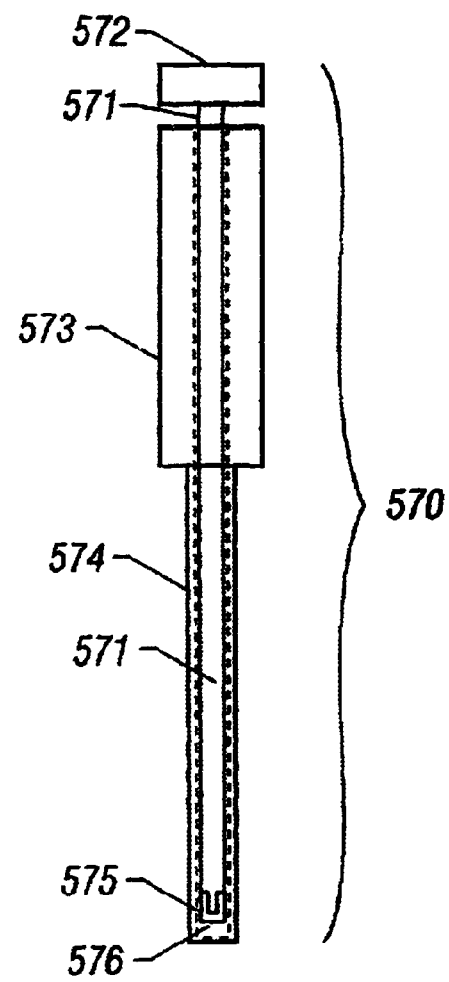
FIG. 9F
FIG. 9G

CARTILAGE REPAIR PLUG

FIELD OF THE INVENTION

This invention relates generally to the field of orthopedic surgery for the repair and replacement of damaged natural cartilage in a living mammal particularly human beings. More specifically, this invention relates to devices, methods, and instruments for the replacement of defective natural cartilage, where the defects are caused by traumatic injury which brings about sudden, acute damage to the cartilage, and/or by disease or the long term effects of unrepaired cartilage injuries, which over prolonged periods of time, cause a chronic deterioration of the cartilage. Still more specifically, the invention relates to an artificial device, made from a biocompatible material, in the form of a cartilage replacement plug, which is used individually or in multiples, to fill void cavities in cartilage created by the resection and removal of damaged or diseased portions of the natural cartilage or to anchor material that is used to fill such cavities; to a method for resecting damaged or diseased portions of natural cartilage and replacing the removed portion of natural cartilage with one or more such artificial cartilage replacement plugs; to a set of instruments for performing the natural cartilage resection and removal procedure to create a void cavity in the cartilage and for performing the artificial cartilage replacement plug implantation procedure; and to a surgical system for orthopedic surgeons which includes a selection of cartilage plugs of various sizes and shapes needed for performing a number of procedures of varying scope and extent, at various body sites, as well as a set of the surgical instruments needed to perform both the defective cartilage removal procedure and the cartilage plug implantation procedure, with all elements being maintained in a sterile environment in a self-contained carrier, ready for surgical use.

BACKGROUND OF THE INVENTION

Human cartilage has very unique properties. It is one of the few a vascular tissues in the body. It serves to prevent bone growth into the articulating surface of joints, which would otherwise interfere with the motion of such joints. Cartilage is semipermeable and receives its nutrients from the synovial fluid which surrounds cartilaginous tissue in articulating joints and which diffuses into the cartilage during motion of the joint. Cartilage itself also possesses viscoelastic and lubricating properties. Materials which are proposed for use in the repair or replacement of natural cartilage must possess physical and mechanical properties which are as close as possible to those of natural cartilage.

Younger persons, ranging in age from children to young adults, often engage extensively in rigorous athletic activities, such as skiing, surfing, football, basketball, and even roller blading, which frequently results in accidents which cause traumatic injury to cartilage, particularly that surrounding the knees, elbows, and shoulders. In the U.S. alone, there are well over 300,000 such injuries per year. Most of these injuries are to the anterior cruciate ligament of the knee, which frequently becomes torn. Younger persons are also occasionally afflicted with arthritic diseases, such as juvenile rheumatoid and osteoarthritis, which cause degeneration of cartilage. Osteoarthritis may also set-in following a traumatic injury to cartilage which is not repaired or is repaired improperly, leading to a further deterioration of the previously damaged cartilage. The extent of the cartilage defect, resulting either from traumatic injury or chronic disease, can vary considerably from a small area to a larger, more widespread area, or even involve all of the cartilage of an entire joint, depending on the extent of the injury or the extent of the spread of the disease. When the defect is caused by traumatic injury and is extensive enough in size to involve a large mass of cartilage, the damage is not capable of self-healing. Heretofore it was not possible to repair extensive cartilage defects. Such damaged cartilage had to be removed and replaced. Often this required complete joint replacement surgery. Cartilage which has become defective through damage caused by traumatic injury from accident, whether sports related or from other causes, such as an automobile accident, as well as cartilage which has become defective as a result of deterioration due to the spread of a chronic degenerative disease, also typically gives rise to and is accompanied by severe pain, especially where the sites of the damage or disease is proximal to or constitutes part of an articulating joint surface, such as the knee. The damaged or diseased portion of the cartilage is usually also accompanied by swelling of the surrounding tissue; and, where an articulating joint is involved, a disruption in the flow of lubricating synovial fluid around the joint often occurs, which, in addition to being a cause of the source of pain, usually leads to further mechanical abrasion, wear, and deterioration of the cartilage itself, finally resulting in the onset of osteoarthritis and complete disablement of the articulating joint, ultimately requiring complete replacement of the joint.

Historically the only choices available to patients with cartilage damage, especially the cartilage of an articulating joint, such as a knee or elbow, were to initially do nothing if the extent of the damage was only relatively minor in scope, which sooner or later usually led to a worsening of the condition and further damage to the cartilage and to the joint itself, with the patient feeling discomfort and pain when using the joint, thus ultimately requiring a complete joint replacement to restore mobility; or, if the extent of the damage was significant to start with, to immediately perform a complete joint replacement. In the case of very young patients, however, complete replacement of a joint is problematic in that the patient's overall skeletal bone structure is not yet fully developed and is still growing, so that the replaced joint may actually be outgrown and no longer be of appropriate size for the patient when their fully matured adult size, stature, and skeletal structure is attained. Moreover, in the past, many replacement knee, elbow joints and shoulder joints have typically had a maximum active useful life of only about ten years, due to wear and tear and erosion of the articulating surfaces of the joint with repetitive use over time, thereby necessitating periodic invasive surgery to replace the entire joint. For a very young patient this meant that they would have to face the prospect for several more such surgeries over their lifetime, notwithstanding progress and improvements in the wearability of materials used for joint surfaces that have been made and continue to be made as new materials are developed.

In recent years a large number of devices and methods for the replacement of defective portions of natural cartilage have been proposed. Some of these have been directed at enabling the repair of larger portions of defective cartilage without having to resort to a full joint replacement, when an articulating joint is involved. Some of the proposed devices are made from natural cartilage which has been self-harvested or harvested from cadaveric sources, some devices are based on composite artificial materials, and some methods involve the growth of new natural cartilage material. A few of the proposed methods for natural cartilage replacement utilize artificial cartilage devices in the form of pre-formed plugs, which are used to fill-in void cavities created by the resection and removal of the damaged or diseased portion of cartilage from the patient.

The various approaches to the problem of cartilage repair and replacement can broadly be divided into those offering a long-term solution, and those offering a short-term solution. Biological approaches involving the growth of new replacement cartilage, either within or without the patient, are generally considered long-term solutions because of the time needed to regenerate the cartilage; while essentially mechanical approaches involving the implant of pre-formed devices or plugs or the in situ formation of cartilage replacement plugs or devices are considered short term solutions because they can usually be effected immediately by surgical procedures which can be completed in a relatively shorter period of time, and which, therefore, are capable of alleviating a patient's accompanying pain and of rehabilitating a patient in a shorter time span. There are, however, several major problems and disadvantages associated with all of the various prior art cartilage replacement devices and methods which have heretofore been proposed.

The use of naturally derived cartilage plugs presents the major problems of lack of availability, limitations on the size of the repair that can be effected, and high potential for infection and transmission of disease. In some instances it has been proposed, for minor cartilage replacement procedures which involve the replacement of relatively small volumes of cartilage, that the cartilage be harvested from the patient by excising a portion of cartilage of suitable size from a donor site on the patient's body. Where the portion of damaged or diseased cartilage that is to be replaced is more extensive, however, such a self-harvesting procedure is not feasible because a sufficiently large plug cannot be extracted from another site without causing damage to or a weakening of the cartilage and underlying bone at the place of harvesting, or when being harvested from a site at or near another articulating joint, without causing damage to the operability of the articulating joint itself at the point of harvesting. Moreover, there are a limited number of suitable locations on the body from which cartilage can be extracted for use elsewhere. Such a self-harvesting procedure actually involves dual surgical procedures of first performing the harvesting procedure at one situs on the patient, followed by the replacement procedure at another situs on the patient. Depending on the age and overall health of the patient, as well as on other considerations, it may not be feasible to perform both procedures at the same time. Moreover, non-medical considerations must be taken into account. Such a dual procedure is time consuming and costly, and may be objected to on cost grounds in some insurance or managed care contexts.

Because the procedures are invasive, there is the additional risk of infection and pain to the patient occasioned by the need for two separate surgical procedures, at the cartilage harvesting site and at the cartilage repair emplacement site.

As an alternative to such a self-harvesting procedure, some have proposed that cadaveric cartilage specimens be extracted and used. This alternative, however, also presents the same problems of limited sources of availability and potential for infection or transmission of disease. In cases where it is necessary to reset larger portions of damaged or diseased cartilage from a patient, although procedures utilizing natural cartilage replacement plugs derived from cadaveric sources are not limited by considerations as to the amount of cartilage that can be excised from a particular location in order to preclude damage to or a weakening of the remaining cartilage and/or the joint, at the donor site, as occurs in a self-harvesting situation, there are still limitations as to the total amount of suitable cartilage that can be harvested from cadaveric sources, and the overall reliability of obtaining acceptable cadaveric cartilage sources at all is not high. In addition to the threat of infection to the recipient patient from other external sources, moreover, care must be taken that there is no chance of transmitting any disease carried by the cadaveric donor to the recipient.

One of the long term methods proposed by the prior art involves the regrowth of replacement natural cartilage material in the void cavity formed by the resection of damaged or diseased cartilage. Attempts have been made to isolate and culture chondrocytes or stem cells in vitro. These cells are then implanted or injected into the cartilage defects in order to promote healing. Another such long-term method utilizes morphogenetic growth factors to inductively stimulate cartilage repair. Some of the obstacles to this latter method involve the selection of one or more appropriate growth factors; the selection of appropriate delivery vehicles for controlled, time-release of the growth factors to ensure that the proper concentration of growth factor is maintained at the implant site; and necrosis of immature or newly regenerated tissue under stress or when subjected to loading conditions.

An example of one such long-term method, and the compositions for effecting the method, is disclosed in U.S. Pat. No. 5,723,331 to Tubo et al. for "Methods and Compositions for the Repair of Articular Cartilage Defects in Mammals". The method involves the use of denuded chondrogenic cells which are proliferated ex vivo as monolayer cultures in order to expand the pool of available chondrogenic cells. The proliferated cells are then seeded in a pre-shaped well having a cell contacting, adhesive surface. These cells redifferentiate and begin to excrete cartilage-specific extra cellular matrix.

The principal disadvantages of this method are that it is very complicated and time consuming, requiring up to several months to fully culture the cartilage cells to the point where they are available for use in a preformed shape. This method also faces the obstacles facing all such long-term methods mentioned above.

In the area of short-term, interim solutions, attempts have been made to repair or resurface cartilage defects with implantable medical devices made from biocompatible materials. For example, the use of collagen sponges has been proposed as an implant to promote cartilaginous tissue ingrowth, however, this method has not demonstrated good long-term success. The use of an injectable liquid polyurethane and poly ethyl methacrylate has also been proposed. These systems are based on arthroscopic injection of the reactive liquid composition at the site of the cartilage defect. The composition then sets in situ. From a practical viewpoint, these methods are limited to those applications where the surrounding cartilage forms a natural cartilage capsule that is capable to acting as a mold to contain and shape the injected liquid composition until it sets. According to some proposed methods, the injected material is capable of being arthroscopically shaped after it has been injected. A major disadvantage of using reactive polyurethane-based systems is that residue diisocyanate in the reactant becomes hydrolyzed in the presence of moisture, to diamine, which is both toxic and carcinogenic.

One such method based on the injection of a reactive polyurethane system with arthroscopic shaping of the injected mass is disclosed in U. S Pat. No. 4,743,632 to Marinovic for "Polyurethane Urea Polymers as Space Filling Tissue Adhesives". According to this method, polyurethane urea polymers are prepared by mixing purified isocyanate polyurethane prepolymers with an aqueous solution of an amino, ureido, or hydroxyl substituted amine or a like-substituted alpha-amino acid. The composition, while still in liquid form, is injected into a cavity where it solidifies.

Another reactive system is disclosed in U.S. Pat. No. 5,556,429 to Felt for "Joint Resurfacing System". The system involves a method that includes the delivery of a curable biomaterial, which is a composite of two or more materials, particularly those comprising two phase systems formed from a polymeric matrix and a hydrogel filler. The polymeric materials include polyurethane, polyethylenes, polypropylenes, polyvinyl chlorides, and others. Matrix materials include silicone polymers and polyurethane polymers. The hydrogels are water-containing gels. The composition is introduced in liquid form, by minimally invasive means, such as by arthroscopic injection, followed by in situ curing of the material, such as by exposing the liquid polymer to ultraviolet light, and shaping and contouring of the cured material, which is also performed arthroscopically.

One of the prior art artificial cartilage replacement devices and methods is disclosed in U.S. Pat. No. 5,067,964 to Richmond et al. for "Articular Surface Repair". The cartilage repair piece disclosed there is a composite which includes a backing layer of non-woven, felted fibrous material, which is conformable to flat and curved surfaces. The front face of the backing layer is either uncoated or covered by a coating of a tough pliable material having a front surface which is tough smooth and slippery in the presence of synovial fluid, so that the device responds naturally at an interface with other cartilage. A disadvantage associated with such approach is inherent in the lack of any physical anchoring to the underlying bone.

A disadvantage and limitation of this method and this type of cartilage replacement device is that it requires cell ingrowth into the felted backing for biologic fixation of the device. This type of soft tissue fixation is less desirable than fixation achieved by bone ingrowth or fixation directly with bone without a fibrous tissue interface. Their device is composed of a layer of polymer attached to a porous felt like backing which may fatigue with motion and result in delamination. Moreover, this type of failure may occur before biologic fixation occurs resulting in failure of the device. In addition, their device is flexible to achieve conformation with the cartilage surface and may not allow adequate weight bearing. In contrast, our device is already stnicturally adequate to withstand full weight bearing immediately without the need to develop biologic fixation.

Instruments for resecting cartilage, such as for excising a plug of damaged or diseased cartilage, are known in the art. U.S. Pat. No. 4,641,651 to Card for "Cartilage Punch and Modified Prosthesis in Tympanoplasty" discloses a cartilage punch for removing a cartilage plug of uniform thickness. The instruments associated with the present invention are customized for effecting the various steps of the procedure according to the present invention, and include instruments for resecting the damaged or diseased cartilage, for shaping the resulting void, and for implanting the replacement cartilage plug.

Published World Intellectual Property Organization Patent Application WO 96/27333 of Hart et al. to Innovative Devices, Inc. for "Apparatus and Methods for Articular Cartilage Defect Repair" discloses a bone plug removal tool that includes a cylindrical cutting element having a external surface and an internal surface defining an internal bore extending along a longitudinal axis of the cutting element from a proximal cutting edge.

Accordingly, there is a need in the art of orthopedic replacement surgery, especially for young patients, of a means of replacing resected portions of damaged or diseased cartilage that does not involve extensive invasive surgery or removal of extensive portions of the cartilage beyond the immediately affected portion; in the case of cartilage that constitutes part of an articulating joint such as a knee or elbow, that does not require a full joint replacement when the joint is still substantially viable and motion of the joint has not been completely compromised; which provides for a readily available source for the cartilage material in unlimited quantities; which does not require the harvesting of the material from the recipient or from cadaveric sources; and which offers simplicity and speed both in the production of the cartilage replacement materials itself and in the actual procedure for its implantation.

OBJECTS OF THE INVENTION

Accordingly, it is an object of the present invention to provide a preformed artificial cartilage replacement device, made from a biocompatible material and fabricated in the shape of a plug, to repair defects in cartilage.

It is a further object of the present invention to provide artificial cartilage replacement devices, which are fabricated as plugs in a variety of sizes and shapes, and which are used to fill a void in cartilage, created by the removal of a defective portion of cartilage of virtually any size and shape, such that the plugs are capable of being utilized either individually, or in a plurality as part of a mosaicplasty.

It is another object of the present invention to provide artificial cartilage replacement devices having mechanical and physical properties that closely match the cartilage being replaced.

It is a still further object of the present invention to provide an artificial cartilage plug which has additional means of anchoring itself to non-defective cartilage and/or bone surrounding the void cavity into which the plug is implanted.

It is another object of the present invention to provide artificial cartilage plugs for anchoring a flowable polymer to the bony base of a lesion site.

It is another object of the present invention to provide artificial cartilage replacement devices that become biologically fixed in place.

It is another object of the present invention to provide an orthopedic surgical procedure for removing a defective portion of cartilage and refilling the void cavity thereby created with one or more artificial, biocompatible, preformed cartilage replacement plugs.

It is yet another object of the present invention to provide a set of surgical instruments used to perform the surgical procedure of removing a portion of defective cartilage and replacing it with an artificial, biocompatible, preformed cartilage replacement plug.

It is still another object of the present invention to provide a self-contained orthopedic surgical cartilage repair and replacement system which includes an assortment of preformed, artificial, biocompatible cartilage replacement plugs of varying sizes, shapes and configurations, together with a set of surgical instruments for performing a cartilage removal and replacement procedure, all maintained under sterile conditions in a portable container, so as to enable an orthopedic surgeon to have all the elements for performing one or more cartilage removal and replacement procedures readily and conveniently available.

It is an overall objective of the present invention to provide a device, method, and instruments to enable the repair of cartilage defects by removing a defective portion of cartilage in a patient and replacing the removed cartilage and filling the void created by the removal of the defective cartilage with an artificial, biocompatible material, such that virtually any size cartilage defect can be repaired in a safe, simple and fast procedure that does not involve a long period of time for cartilage regrowth and does not involve the performance of multiple invasive surgical procedures on the patient.

SUMMARY OF THE INVENTION

The present invention includes a preformed, presized, and preshaped cartilage replacement plug, made from a biocompatible, artificial material, which is used, either individually or in combination with other such plugs, depending on the volume of cartilage to be replaced, to replace a portion of damaged or diseased cartilage which has been resected, thereby filling the void left by the resected cartilage. Alternatively, certain embodiments of such plugs may be employed to serve as anchors for a flowable polymer that is used to fill the void. The invention also includes a procedure for removing the portion of damaged or diseased cartilage and for implanting the replacement artificial cartilage plug or plugs. The invention still further includes a set of instruments for effecting the procedure and a complete system for orthopedic surgeons which includes a selection of artificial replacement cartilage plugs of varying sizes and shapes suitable for a variety of applications and specific procedures, together with a complete set of the instruments used to resect the damaged or diseased cartilage and for implanting the replacement plug or plugs, all in a self-contained carrying case.

Because the material of the cartilage replacement plugs of the present invention is artificial, there are no limits as to its availability and because the material is biocompatible and is kept sterile prior to use, there is no danger of the cartilage plugs of this invention being rejected when in the body, or of transmitting any disease or infection. Due to the ready availability of the cartilage plugs of this invention and the relative simplicity of the procedure for implanting them, there is no need for any dual invasive surgical procedures being performed on the recipient, including any kind of initial harvesting procedure, in addition to the actual cartilage replacement plug implantation procedure, but only the implantation procedure itself. The threat of transmission of disease from a donor source is thereby effectively eliminated, the overall risk of infection to the patient is greatly reduced and the overall costs of the procedure are kept to a minimum.

The cartilage plugs according to the present invention are fabricated from a biocompatible material which is easy to preform, presize and preshape. They can be formed and contoured in essentially any shape and size depending on the particular application for which they are to be used. Biocompatible polymeric materials such as biostable polycarbonate polyurethanes are particularly well suited for use. The cartilage plugs can be fabricated from a wide variety of synthetic and natural polymeric materials.

In preferred embodiments of the present invention, the plugs are formed of a lamination of a number of various materials each having different mechanical and physical properties. More particularly, a material having properties similar to that of subchondral bone is selected for use in the layer of the plug that is to be positioned adjacent or within the subchondral bone while another material, having properties similar to hyaline cartilage is selected for use in the layer of the plug that is to be positioned on the surface of the repair. A third material selected for having properties similar to natural cartilage forms the bulk of the plug and is positioned between the bone-like and hyaline cartilage-like materials. Alternatively, one of the three materials may be deleted or more than three materials may be combined in the lamination.

In additionally preferred embodiments, ridges are formed about the periphery of the plugs to facilitate a mechanical interlocking with the surrounding natural cartilage, with bone and/or with one another. Such ridges may define parallel planes, each perpendicular to the central axis of the plug. Alternatively, the ridges may comprise a single helix extending about the plug's central axis. The ridges may be continuous or may be segmented, confined to certain areas of the plug's exterior. The cross-section of each such ridge may be symmetrical or may define a barb-like protuberance that eases insertion but resists retraction.

Additionally preferred embodiments of the present invention include plugs that have a hollow interior. A void formed in the interior of the plug may extend partially into the interior of the plug to varying degrees or may extend completely therethrough. Additionally, ridges may optionally be formed on the interior surface of such voids in various configurations. Such plugs are preferably employed as anchors in conjunction with a flowable polymer. The voids serve to more positively fix the polymer to the plug once the polymer has cured.

Preferred embodiments of the plugs of the present invention may be formed with roughened and/or porous surfaces. Asperity and pores within a certain size range facilitate cell ingrowth that results in biologic fixation. Larger pores are useful when the plug is used as an anchor in conjunction with a flowable polymer wherein an influx of the polymer into the pores facilitates a mechanical fixation thereto upon curing.

Finally, the plugs of the present invention may be formed in any of a large number of different geometric shapes ranging from cylindrical to polyhedral. The plug may be of constant or of variable diameter as for example a truncated cone.

These and other features and advantages of the present invention will become apparent from the following detailed description of preferred embodiments which, taken in conjunction with the accompanying drawings, illustrate by way of example the principles of the invention.

BRIEF DESCRIPTION OF THE DRAWINGS

FIG. 1 is a greatly enlarged perspective view of a preferred embodiment of the present invention;

FIG. 2 is a greatly enlarged perspective view of an alternative preferred embodiment of the present invention;

FIG. 3 is a greatly enlarged perspective view of another alternative preferred embodiment of the present invention;

FIG. 4 is a greatly enlarged perspective view of another alternative preferred embodiment of the present invention;

FIGS. 9a–g show instruments for effecting a defective cartilage resection and replacement cartilage plug implantation procedure according to the present invention;

DETAILED DESCRIPTION OF PREFERRED EMBODIMENTS

Definitions

Figure 5:
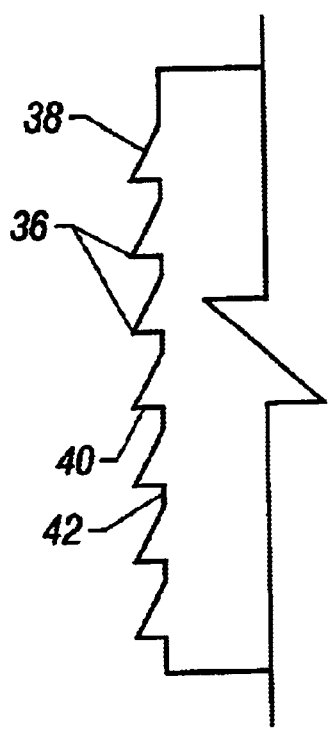
FIG. 5 is a partial cross-sectional view taken along lines 5—5 of FIG. 4.

As used herein, the following words and terms shall have the meanings ascribed below:

"distal" refers to the end of a cartilage replacement plug which is inserted into the void and is nearest to the subchondral layer of bone;

"proximal" refers to the end of a cartilage replacement plug which is nearest to the surface of the surrounding cartilage;

"equilateral" means having a plurality of linear sides or edges, all of which are equally identical in length.

"congruent" means, with respect to three-dimensional figures that any two such three dimensional figures are completely superposable throughout, about all three dimensional axes, that is, both figures have identical corresponding three dimensional angles and equilateral sides or edges, i.e., the two figures are both equiangular and equilateral; and, with respect to two-dimensional, planar figures, that any two such two-dimensional, planar figures are completely superposable throughout, about both planar axes, that is, both figures have identical corresponding internal angles and equilateral sides or edges, i.e., the two figures are both equiangular and equilateral.

"similar" means, with respect to three-dimensional figures, that any two such three-dimensional figures have identical shapes, but are not superposable in that they have different sizes, that is, both figures have identical corresponding three-dimensional angles, but corresponding sides or edges of proportionately different lengths, i.e., the two figures are equiangular but not equilateral; and with respect to two-dimensional, planar figures, that any two such two-dimensional, planar figures have identical shapes, but are not superposable in that they have different sizes, that is, both figures have identical corresponding internal angles, but corresponding sides or edges of proportionately different lengths, i.e., the two figures are equiangular but not equilateral.

"curviplanar" means a planar surface existing in three-dimensional space, and which may be a plane which is arcuate or curved, undulating (i.e., has a sinusoidal wave shape), or which is closed on itself and continuous about an axis. The side surface of a circular cylinder, between the two circular faces of the cylinder, is an example of a curviplanar surface which is closed on itself and continuous about an axis which is the circumference of the surface.

"polyhedron" means a three-dimensional geometrical shape formed by the intersection of a plurality of flat planar surfaces or a three-dimensional geometrical shape formed by the intersection of one or more flat planar surfaces and at least one curviplanar surface that is closed on itself so as to be continuous.

"regular" means, with respect to a three-dimensional geometrical figure, composed of a plurality of flat planar two-dimensional surfaces, each such flat planar two-dimensional surface having a defined shape, a situation wherein all of the component flat planar two-dimensional surfaces of the three-dimensional geometrical figure have the same shape and are both congruent and identical, that is, all component flat planar two-dimensional surfaces are both equiangular and equilateral; and, with respect to a plurality of flat planar two-dimensional geometrical surfaces having the same shape, which constitute parts of the same three-dimensional geometrical figure, together with one or more other flat planar two-dimensional surfaces or at least one curviplanar surface that is closed on itself so as to be continuous, having a different shape or shapes from the plurality of flat planar two-dimensional geometrical surfaces having the same shape, a situation wherein all such flat planar two-dimensional geometrical surfaces having the same shape, are both congruent and identical, that is, all such flat planar two dimensional geometrical surfaces having the same shape are both equiangular and equilateral.

"irregular" means, with respect to a three-dimensional geometrical figure, composed of a plurality of flat planar two-dimensional geometrical surfaces or a combination of a plurality of flat planar two-dimensional geometrical surfaces and at least one curviplanar geometrical surface that is closed on itself so as to be continuous, a situation where at least two of said flat planar two-dimensional geometrical surfaces have the same shape and are both congruent and identical, that is, said at least two flat planar two-dimensional geometrical surfaces are both equiangular and equilateral; and, with respect to a plurality of flat planar two-dimensional geometrical surfaces, which constitute parts of the same three-dimensional geometrical figure, a situation where at least two of said flat planar two-dimensional geometrical surfaces have the same shape and are both congruent and identical, that is, said at least two flat planar two-dimensional geometrical surfaces are both equiangular and equilateral.

"completely irregular" means, with respect to a three-dimensional geometrical figure, composed of a plurality of flat planar two-dimensional geometrical surfaces or a combination of a plurality of flat planar two-dimensional geometrical surfaces and at least one curviplanar geometrical surface that is closed on itself so as to be continuous, a situation where no two of said flat planar two-dimensional geometrical surfaces have the same shape, or, if they are similar and have the same shape, are not also both congruent and identical, that is, if two or more flat planar two-dimensional geometrical surfaces are similar and have the same shape, they are not also equilateral; and, with respect to a plurality of flat planar two-dimensional geometrical surfaces, which constitute parts of the same three-dimensional geometrical figure, a situation where no two of said flat planar two-dimensional geometrical surfaces have the same shape, or, if they are similar and have the same shape, are not also both congruent and identical, that is, if two or more flat planar two-dimensional geometrical surfaces are similar and have the same shape, they are not also equilateral.

"symmetrical" means, with respect to a three-dimensional figure, one in which a plane bisecting the figure along any axis creates two half-figures which are mirror images of one another; and, with respect to a two-dimensional figure, one in which a plane bisecting the figure along any axis creates two half, planar, two-dimensional figures which are mirror images of one another.

"asymmetrical" means, with respect to a three-dimensional figure, one in which a plane bisecting the figure along at least one axis creates two half figures which are not mirror images of one another; and, with respect to a two-dimensional figure, one in which a plane bisecting the figure along any axis creates two half, planar, two-dimensional figures which are not mirror images of one another.

"polygon" means a two-dimensional flat planar surface forming a defined, closed shape bounded by a plurality of sides or edges of the polygon.

"chord" means, with respect to a regularly shaped closed curvilinear planar surface figure, the longest straight line between any two points on the circumference of the closed curvilinear planar surface figure which also passes through the geometric center of the figure.

"right" means, with respect to a cone or a pyramid, respectively, a conical or a pyramidal shape wherein a straight line between the apex of the cone or pyramid and the geometric center of the base is perpendicular to the plane of the base, and forms a pair of right angles at the intersection therewith; and, with respect to a cylinder or a frustum of a cone or pyramid, respectively, a cylinder of or a frustum wherein the a straight line between the geometric centers of the first and second faces of the cylinder or frustum is perpendicular to the plane of each face, and forms a pair of right angles at the intersection with each plane.

"oblique" means, with respect to a cone or a pyramid, respectively, a conical or pyramidal shape wherein a straight line between the apex of the cone or pyramid and the geometric center of the base is not perpendicular to the plane of the base and forms a pair of non-right angles at the intersection therewith, including one acute angle and a complementary obtuse angle, which together form a straight angle; and, with respect to a cylinder or a frustum of a cone or pyramid, respectively, a cylinder or a frustum wherein a straight line between the respective geometric centers of the first and second faces of the frustum is not perpendicular to the plane of either face, and forms a pair of non-right angles at the intersection with each plane, each pair including one acute angle and a complementary obtuse angle, which together form a straight angle.

"parallel" means, with respect to a frustum of a cone or a pyramid, a frustum of a cone or a pyramid wherein the first and second planar faces of the frustum lie in parallel planes.

"non-parallel" means, with respect to a frustum of a cone or a pyramid, wherein the first and second planar faces of the frustum do not lie in parallel planes, but lie in intersecting planes.

"flowable polymer" means a polymer that, when initially placed int the application site or mold at the time of use, has reactive components in the prepolymerized or early polymerization state and is physically fluid or flowable but is capable of curing (polymerizing) to a solid state relatively quickly after application.

"natural polymer" means any of a variety of long chain molecules that have repeating structural units that are derived from biologic (cellular) synthesis. Examples include collagens, gelatins (denatured collagen), fibrin, alginates, etc.

"synthetic polymer" means any of a variety of long chain molecules that consist of a number of repeating structural units that are derived from laboratory chemical synthesis.

In its most basic form, the cartilage replacement plug device according to the present invention is fabricated by molding biostable polycarbonate polyurethane material into preformed shapes. A single such material may be used to form a plug or anchor plug or, alternatively, a number of different such materials may be combined as a lamination.

The cartilage plug of the present invention has a polygonal or circular cross-section, with a height-to-diameter ratio of from about less than one to one to about 20:1. The plugs may be molded in a wide range of sizes and having various height-to-diameter ratios in order to accommodate a wide range of cartilage replacement situations. Thus, the generally round devices have shapes ranging from flat disks to cylinders. A variety of factors must be taken into consideration for each particular application, such as the location where the cartilage replacement plug or plugs are to be implanted, the size of the cartilage defect that is to be repaired, and the size and shape of the void cavity, either as initially formed by resection of the defect, or by any subsequent surgical contouring of the cavity, into which the cartilage replacement plug is to be implanted. Cartilage replacement plug devices having a flattened, disk shape are most suitable for more extensive but shallow defects, while devices having a large height-to-diameter ratio are suitable for defects having a smaller surface area, but which extend deeper into the cartilage and/or the subchondral bone layer.

The generally cylindrically-shaped family of basic cartilage replacement plugs according to the present invention are characterized in that they have uniformly sized and shaped circular end surfaces which are connected by a single continuous cylindrical side surface between the end surfaces. In these embodiments, the side surface is perpendicular to both of the end surfaces, with the side and end surfaces forming right angles with one another. Cartilage replacement plugs according to the present invention are generally fabricated as solid elements, but may alternatively be fabricated as hollow elements as long as they retain overall mechanical properties, such as strength and load bearing ability, similar to those of the natural cartilage which they are replacing.

The plugs of the present invention may optionally be configured to serve as anchors for a flowable polymer that is subsequently introduced into the cavity. Such anchors are positioned so as to be partially embedded within the subchondral bone while a portion of the plug remains protruding above the surface of the bone. The protruding portion serves as a fixed element to which the curing polymer can bond and which provides a mechanical interconnection between the bone and the polymer. In order to enhance the anchoring ability of the plug, the exterior of the plug may be formed with ridges, the plug may have a hollow interior to receive the polymer and such hollow interior surfaces may have ridges formed thereon.

The surfaces of the cartilage plugs of the present invention may be treated so as to expose a porous or roughened surface. By treating the surface of the plug such that it is roughened or textured, cell attachment is enhanced and allows for cell migration and overgrowth of a tissue layer.

With appropriate surface asperity, the resultant cells adhere via ongrowth and ingrowth into the surface of the plug enhancing fixation. Such cell ingrowth may be ultimately transformed into a bony interface with the plug and is considered a desirable characteristic. Important in this transformation is how load is transferred from the device to the surrounding tissue. A large mismatch in deformation between the plug and surrounding tissue can lead to a fibrous tissue layer around the plug that, although flexible, does not provide the desired fixation. Porosity, like asperity, can be important and beneficial when considering biologic fixation. A porosity that is too small, i.e. equal to or smaller than 10 micrometers, can inhibit cell ingrowth and results in no biologic fixation. A porosity that is too large, i.e., equal to or greater than 1–2 mm, results in less cell filling of the porous voids and poorer biologic fixation. However, a large porosity may be beneficial if used in an anchoring application for synthetic or natural polymer. Sufficiently large pores allow the influx of the polymer while in its flowable state and facilitates a mechanical fixation upon curing.

FIG. 1 shows a cartilage plug 12 according to the present invention which has a circular cross-section and end surfaces 14 and 16, with the side 18 and end surfaces being perpendicular to one another while FIG. 2 illustrates a tapered embodiment 20 of circular cross-section. Other embodiments 22 of cartilage plugs with circular cross-sections include oblique shapes wherein the side 24 and end surfaces 26, 28 are not perpendicular to one another but intersect at an angle other than a right angle as is shown in FIG. 3.

Cartilage replacement plugs according to the present invention having such an oblique configuration are suitable for replacing defects, most often those resulting from a chronic disease condition in which the defect has penetrated into the cartilage in a pattern which does not extend down into the cartilage at a right angle to the outer end surface of the defect, but which may extend obliquely into the cartilage from the surface. Rather than having to resect a portion of cartilage that is greater in surface area at the outer surface than is necessary in order to get to the off-centered base of the defect, it is less invasive to remove a defect core which is not at a right angle to the outer surface, and which extends obliquely into the cartilage. These oblique void cavities are easily filled by uniquely shaped cartilage replacement plugs.

A basic cartilage plug according to the present invention is not, however, limited to having a cylindrical shape with circular end surfaces. Other configurations for the basic cartilage replacement plugs of the present invention include shapes having oval, ovoid, elliptical, and irregular closed curvilinear (i.e., curviplanar) shaped end surfaces, with a correspondingly shaped continuous closed side surface. Cartilage plugs with non-circular curviplanar end surfaces may also be fabricated as straight sided or obliquely sided elements.

Still other basic cartilage plugs according to the present invention include polyhedra having polygonal cross-sections and end surfaces with from three to twenty or more edges and rectangular sides, instead of circular ends and a single continuous, curved, cylindrical side surface. Irregular polygonal shapes may also be used for the end surfaces of such plugs instead of those having a set number of equal side edges. Typically, the polygonal end surfaces for the cartilage replacement plugs range from three-sided triangles to twelve-sided dodecahedrons. Although polygons having a greater number of sides than twelve may be fabricated within the scope of the invention, the difficulty of molding such embodiments and the related cost of making them exceed any advantage of being able to more closely fit a void cavity in the cartilage. It is generally easier to recontour the shape of the void cavity to accommodate one of a standard set of plug shapes, than to produce a plug having a custom shape. For cartilage plugs having polygonal shaped end surfaces, it is particularly preferred to fabricate them having either four-sided square or rectangular ends, the six-sided hexagonal ends 30, 32 shown in FIG. 4 or eight-sided octahedral ends.

According to another preferred embodiment, a cartilage plug of the present invention may also be shaped with a taper towards its distal end as is shown in FIG. 2. In this embodiment, the distal end surface 34 is congruent to the proximal end surface 36, but is proportionally smaller, so that the side walls 38 of the plug taper inward toward the distal end of the plug. It has been found that such tapered plugs remain in place in the cavity into which they have been implanted better than straight-sided plugs wherein both the proximal and distal end surfaces are the same size and the side walls of the plug are all parallel and form right angles with both end surfaces. The taper can range from 0 to 15 degrees. The cartilage plugs may also be fully tapered at one end to a point, so that, in the case of a cartilage plug with a circular end surface, the plug has a conical configuration, and in the case of a plug having a polygonal end surface, the plug has a polygonal pyramid configuration.

According to still other embodiments, the cartilage plugs according to the present invention may have tapered sides and still retain congruent end surfaces of different sizes so that the plug has the shape of a frustum of a cone in the case of a plug with circular or other rounded end surfaces, and the shape of a frustum of a polygonal pyramid having polygonal end surfaces.

It has been found that, in general, disk-shaped and cylindrical cartilage replacement plugs are the easiest to mold and have been found to be best suited for use in the repair of small to medium sized defects which are effectively repaired using a single plug. It has additionally been found that plugs with tapered sides or obliquely configured plugs have the best adhesion to the walls of the surrounding void cavity into which the plugs are implanted. Generally, the deeper the plug and the higher the height-to-diameter ratio, the better the plug remains in place in the void cavity. Flatter, shallower, disk-shaped plugs have a greater chance of becoming loose in the cavity.

Figure 6:
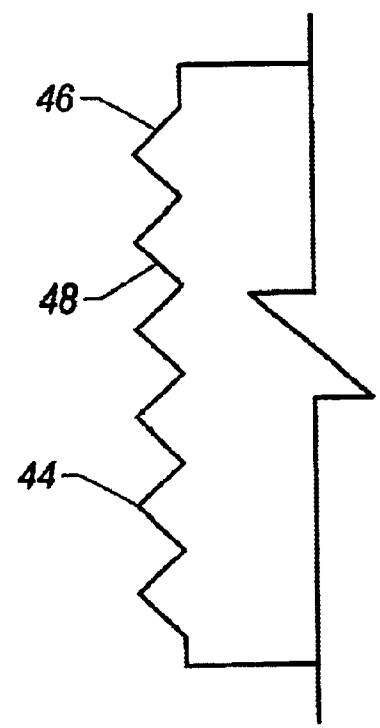
FIG. 6 is a partial cross-sectional view similar to FIG. 5 of an alternative embodiment of the present invention.
Figure 7:
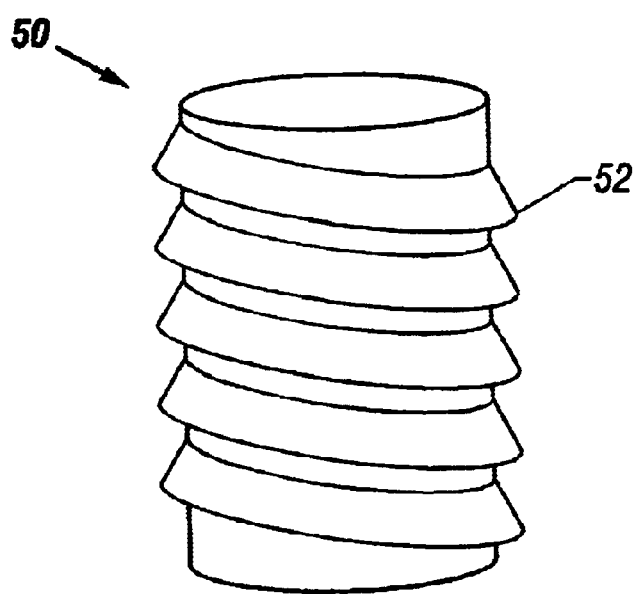
FIG. 7 is a greatly enlarged perspective view of another alternative preferred embodiment of the present invention.

In order to improve the anchorability of plugs and prevent them from coming loose, the cartilage replacement plugs of the present invention may also have additional features to help anchor them to adjacent cartilage and/or adjacent plugs so as to hold them in place within the void cavity into which they are implanted. These additional features include ridges that are formed on the side surfaces of the plugs. The ridges may be discretely situated at various points on the sides of the plugs, or they may form a continuous band spirally wound around the side surface of the plug, or forming a series of separate, discrete, parallel bands around the side of the plug. FIG. 4 illustrates a plug 34 having a series of parallel ridges extending about its hexagonal periphery. The cross-sectional view (FIG. 5) shows that the ridges 36 have abarbed configuration wherein the distal side 38 of each ridge is gently sloped while the proximal side 40 has a steeper angle, which in this embodiment is substantially perpendicular to the side 42 of the plug. FIG. 6 illustrates the cross-section of another embodiment wherein the ridges 44 comprise ribs that have similarly sloped distal 46 and proximal 48 sides. FIG. 7 illustrates yet another alternative embodiment 50, wherein the ridges 52 comprise a single helix that spirals about the periphery of the plug. Ridges maybe formed on any of the plug configurations of the present invention, including configurations having circular or polygonal cross-sections or with tapered side surfaces or oblique end surfaces.

The barbs and ribs, either as a plurality of individual such elements, or as a single continuous, spiral band or a series of parallel rings or bands of barbed or ribbed elements, may be fabricated as an intrinsic part of the plug during the original injection molding process, or alternatively, they may be added to a basic, smooth-sided cylindrical plug, such as by machining, gluing or otherwise fusing them to the side surface of the plug, after the basic plug has been formed. It is preferable, however, that the barbs or ribs be formed as an intrinsic part of the overall plug when it is molded to ensure that the elements afford the maximum anchoring contact between the plug and the surrounding cartilage, and that the elements do not themselves come loose from the main side body of the plug over time as might eventually occur if they are simply glued to the plug.

It is also possible to anchor the cartilage replacement plug to the base of the cavity into which it is being implanted through use of a fastening element which penetrates into the underlying cartilage or subchondral bone layer, depending on the depth to which the plug is implanted. Such fastening or anchoring element may be in the form of a nail or screw which holds the plug to the base of the cavity.

Although there is no limit to the size of single plugs which may be made according to the present invention, and even large defects can be filled using plugs fabricated to have a sufficient size and volume capable of filling large voids, it has been found that it is easier to fill large voids in cartilage created by the removal of defective cartilage with a plurality of cartilage replacement plugs, each made of a smaller size and standard shape.

A plurality of cartilage plugs are used to fill larger void in what is known as a mosaicplasty. In such a procedure, a plurality of from two to twenty individual cartilage plugs are used to fill substantial voids. Although a mosaicplasty procedure may be carried out using individual cartilage plugs of any shape, including the disk or cylindrical shapes frequently used for single plug replacement procedures, and although a variety of different shaped and sized plugs may be used in such a mosaicplasty procedure, such a procedure works best when plugs having polygonal shaped end surfaces are utilized so that the side surfaces of adjacent plugs in the mosaic can fit tightly up against one another. When round end surface plugs such as disks or cylinders are used in a mosaicplasty, interstitial void spaces between adjacent plugs remain. Although various types of fillers, such as bone cement or polyurethane, may be used to fill-in these interstitial voids, that step further complicates the procedure. Alternatively, such interstitial voids may be left open for natural ingrowth, however, that takes a considerable period of time and may not occur uniformly, particularly near the inner sections of the mosaic of plugs. Natural subchondral bone and cartilage regrowth around the outer edges of the mosaic, that are in contact with the adjacent natural cartilage and bone may occur relatively faster, but nevertheless would be at a slow pace. If such interstitial voids are allowed to remain due to lack of infilling, or due to awaiting natural ingrowth, the integrity of the mosaicplasty of plugs may become compromised over time due to the plugs loosening in place. One alternative way of overcoming this is to have the side surfaces of the plugs fitted with an interlocking "tongue and groove" mechanism or the like which holds adjacent plugs tight with respect to one another.

According to yet another preferred embodiment of the invention, a cartilage replacement plug may be fabricated as a multi-layer composite structure formed from several layers 54, 56, 58 of different materials. One embodiment of such a plug 12 (FIG. 1) is made with three layers of different materials which are fused or bonded together. A first layer 54, at the distal end of the device, which upon implantation is closest to the subchondral bone layer, is made from biostable polycarbonate polyurethane 75-D, a material having an elastic modulus similar to subchondral bone. An intermediate 56, central layer of the device is made from polycarbonate polyurethane 55-D, which has properties similar to natural cartilage. A third layer 58, at the proximal end of the device, which is closest to the surface of the cartilage surrounding the implanted plug, is made from polycarbonate polyurethane 80-A or a thermoplastic hydrogel coating, which has properties similar to those of hyaline cartilage, which is the type of cartilage which occurs nearest to the outer surface of an articulating joint, and is lubricated by the synovial fluid. Other combinations of materials may be employed to more accurately duplicate the stiffness characteristics of the native cartilage. Materials of construction for such a multi-layer cartilage replacement plug may further include polyurethane adhesives that contain non-leachable isocyanate groups that are used to bond the multiple layers together, and injectable polyglyceryl methacrylate hydrogels with viscoelastic and lubricious properties. Intermediate layers may be relied upon to provide a desirable load transfer between upper and lower layers of different hardnesses. A layer may also be developed through solvent polymer-hydrogel treatment of the exposed articulating surface of the plug device thereby imparting a hydogel coating with good lubricity. FIGS. 2 and 3 illustrate an alternative embodiment wherein only two different materials 60, 62 and 64, 66 are combined in a lamination.

The dimensional proportions of polymer layers for construction of a plug in accordance with the present invention may vary widely to accommodate various applications. In an embodiment wherein the 50% of the plug is to be embedded in the bone, the base layer with the hardest material would comprise about 50% of the length of the plug while the softest superficial layer which will interface with opposing articular cartilage surface may comprise about 33% of the total length of the plug. The intermediate layer, of intermediate softness, may therefore comprise about 17% of the total length of the plug.

The advantages to the multi-layer construction include a more physiologic load transfer to the underlying subchondral bone. This is achieved through the plug having zones of differing mechanical and physical properties. The result enhances the stability of the implant and the cartilage surrounding it.

Figure 8A:
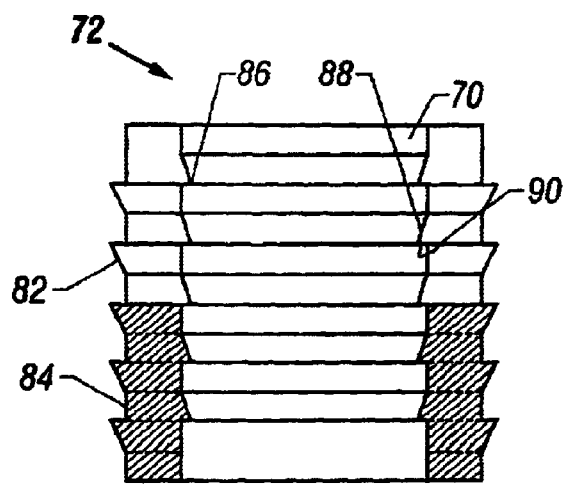
FIGS. 8a–c are greatly enlarged cross-sectional views of alternative preferred embodiments of the present invention.
Figure 8B:
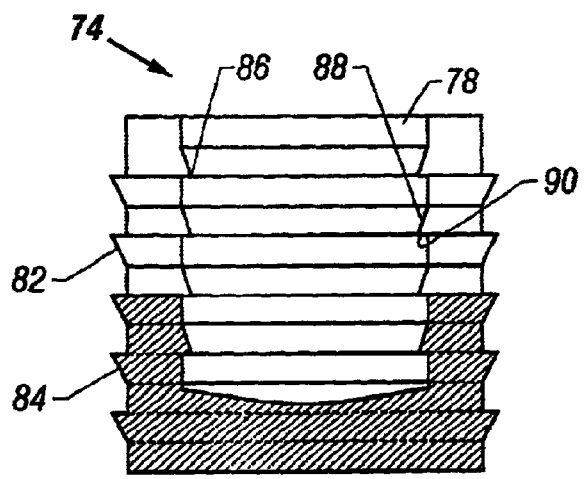
Figure 8C:
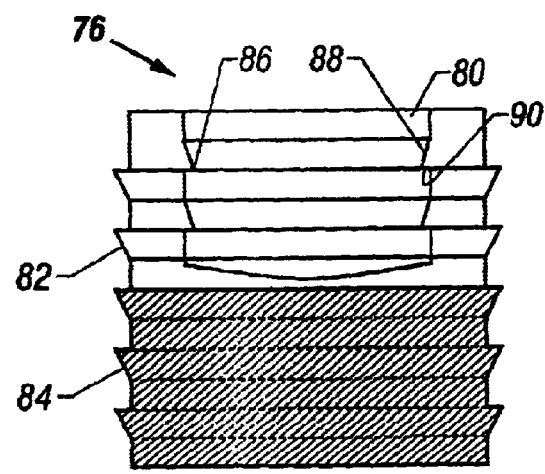

FIGS. 8a–c illustrate alternative preferred embodiments of the present invention wherein a bore is formed in a cartilage plug. FIG. 8a illustrates an embodiment wherein an axial bore 70 extends completely through the plug 72, while FIGS. 8b and 8c show plugs 74, 76 that have bores 78, 80 formed therein that extend well into the interior of the respective plug but do not extend all the way therethrough. The particular plugs that are shown employ two layer laminates 82, 84 and while the bore 78 of plug 74 shown in FIG. 8b extends through the top layer and partially into the second layer, bore 80 of plug 76 shown in FIG. 8c extends exclusively into only the top layer. The bores of these particular embodiments additionally have ridges 86 formed therein. The ridges have a barbed configuration wherein the upwardly facing slope 88 of the ridge is gentle while the downwardly facing slope 90 is substantially perpendicular to the wall of the bore. The ridges formed in the interior of the bores may optionally be symmetrical to define ribs and the ridges may further optionally have a helical configuration winding along the interior of the bore. As a further alternative, the interior wall of the bore may be smooth.

The following described methods are examples of how a laminated plug of the present invention may be manufactured.

Method 1

Extruded rods of biocompatible medical grade polyurethane polymer are available from a variety of commercial vendors specializing in this polymer. Furthermore, such rods are available in different hardnesses and elastomeric properties, e.g. 55 Shore D. Two rods of two different hardnesses, referred to as rod hardness 1 (RH1) and rod hardness 2 (RH2) are selected. In a preferred embodiment, the RH1 rod has a hardness H1 that closely matches mechanical properties of native articular cartilage while the RH2 rod has hardness H2 that closely matches mechanical properties of trabecular bone. For machining purposes, and because said rods of hardness H1 and H2 can be soft and pliable and may not cut when subjected to standard lathe machine turning techniques, the rods may be deep frozen to stiffen them for lathe turning and machining. Once the RH1 rod is frozen, it is placed in a lathe chuck and the exposed end that is perpendicular to the long axis of the rod is radius faced to match any of a variety of predetermined curved surfaces that match the curve surface of the target articular cartilage that is being replaced. The radius-faced surface is identified as surface SA. A cylinder blank is then formed by cutting off the end portion of the said rod RH1 at a predetermined length using a cutoff tool forming a flat bottom surface of the cylinder identified as surface SB.

The H2 rod is deep frozen and similarly chucked for turning but its surface parallel to the long axis is surface machined to form the desired ridges in the form of ribs or barbs, after which the exposed end surface that is perpendicular to the long axis of the rod is faced off with a flat surface identified as SC. The exposed end that is perpendicular to the long axis of the rod is faced forming a surface that is perpendicular to the long axis of the RH2 rod and forming a flat surface identified as SC. A cylinder blank is then formed by cutting off the end portion of the RH2 rod at a predetermined length using a cutoff tool forming a flat bottom surface of the cylinder identified as surface SD.

The surface SB of the RH1 rod is to be mated and permanently joined with surface SC of the RH2 rod. The joining process can be accomplished in a variety of ways. A preferred iteration involves placing said cylinder blank with hardness H1 and cylinder blank with hardness H2 each in a holding collet. The surface SC and SB that are to be joined are treated with a suitable adhesive glue that will bond the two cylinders together. Such adhesive glues may include but are not limited to cyanoacrylates, methylacrylates, octylacrylates, polyurethane solvents, visible or UV light activated adhesives that are commercially available. Glues may be spread thinly and evenly over the surface SC and SB or placed in a suitable pattern of glue dots that results in an evenly spread distribution without glue flashing. The rod cylinders are placed in an alignment guide clamp assembly and the surface SC and SB brought together for glue bonding. After bonding the laminate structure is ultrasonically cleaned and rinsed and prepared for packaging and sterilization.

An alternative method to bond the said two cylinder interface surfaces SB of RH1 and SC of RH2 together include the generation of heat at the SC and SB interface causing the interface to fuse the two surfaces together. The method to generate heat may include but is not limited to the use of focused ultrasonic waves energy at the said interface surface forming a fusion weld. After bonding the laminate structure is ultrasonically cleaned and rinsed and prepared for packaging and sterilization.

Another method involves treatment of said surface SC and SB with a dark pigment such that laser light energy may be absorbed creating an intense heat and shock wave thereby fusing the interface together. After bonding the laminate structure is ultrasonically cleaned and rinsed and prepared for packaging and sterilization.

Yet another method involved the treatment of said surface SC and SB with a powdered metal or fine wire paste that can react with microwaves energy with said metallic elements absorbing the energy creating sufficient heat such that a fusion of the interface occurs. After bonding the laminate structure is ultrasonically cleaned and rinsed and prepared for packaging and sterilization.

Similar methods may be employed to form laminates having three or more layers. Alternatively, an 80-A material may be the sole polymer used, may be used in conjunction with the 55-D material and/or a hydrogel material may be applied thereto to form an additional layer.

Method 2

A metal casting block is prepared as a mold that has the desired dimensions of the final plug geometry. It is envisioned that said mold has a base plate and at least two components that form the walls of said plug. For orientation, said base plate forms the surface on the plug representing the surface of the target articular cartilage that is being replaced. Such mold also has machine cuts for all fixation barbs or ribs that are part of the polyurethane plug. In this iteration, the base plate of the mold is designed to have a curved sulcus which corresponds to the surface curve of the articular cartilage at the target implantation site. This approach requires multiple molds that provide curves that match the potential implantation site. Alternatively, the base plate may be flat and the resultant cast plug is machined in a secondary procedure to attain the desired surface curvature.

In practice, biocompatible polyurethane polymer beads of appropriate hardness are obtained from a commercial source that specializes in this product. The polymer beads are obtained in two hardnesses H1 and H2. The polymer beads H1 (for example 55 Shore D) is harder than H2 polymer beads (for example 80 Shore A). An appropriate mass of H1 polymer beads are placed at base of mold for the first layer (L1) of said plug. An appropriate mass of H2 polymer beads are placed in the mold on top of the H1 polymer beads to from the second layer (L2). The mold is then transferred to the vacuum oven. Vacuum and heat are applied to accomplish the melting and fusion of said beads thereby forming the desired laminate structured plug. After the molding process is complete, the mold is removed from the oven and the mold disassembled to release said plug. The plug is then ultrasonically cleaned and rinsed and prepared for packaging and sterilization.

In an alternative method, a metal casting block is prepared as a mold that has the desired dimensions of the final plug geometry as set forth above. In this iteration, the mold has sufficient structural dimensions to make it compatible with compression molding standards and can be assembled to standard compression molding equipment. It is envisioned that the mold connects to the polymer ram piston assembly that delivers the compression and heat energy for the molding cycle. The compression cycle on the polymer should be matched so that heat from compression is sufficient to fuse the polymer bead raw material.

In practice, biocompatible polyurethane polymer beads of appropriate hardness are obtained from a commercial source that specializes in this product. Such polymer beads are obtained in two hardnesses H1 and H2. The H1 polymer beads (for example 55 Shore D) are harder than H2 polymer beads (for example 80 Shore A). An appropriate mass of H1 polymer beads followed by an appropriate mass of H2 polymer beads are loaded in the supply hopper of the ram piston such that said ram piston forces both H1 and H2 polymer beads simultaneously and in a serial manner into the mold cavity. In the preferred iteration, the speed and force of said ram piston generates sufficient heat to cause fusion of the polymer beads. The mold is then cooled and the completed plug is then removed from the mold assembly. Said plug is ultrasonically cleaned and rinsed and prepared for packaging and sterilization.

Alternatively, a metal injection molding block is prepared having multiple interconnected plug mold voids each having the desired dimensions for producing the final plug geometry including all fixation barbs or ribs. Such mold has a capability for at least dual polymer injection. The injection mold may be so designed that the two inflow pathways for the two polymers are at opposite ends of the plug mold and the outflow pathway at the desired interface level. Alternatively, the injection mold may be designed with a single inflow pathway at the base of the plug mold for both polymers that will be serially injected and a sincle outflow pathway at the opposite end of the plug mold. In these iterations, the articular cartilage end of said plug may be molded with a flat or a near flat curve that can be secondarily machined to achieve the final curvature that corresponds to the surface curve of the articular cartilage at the target implantation site.

In practice, biocompatible polyurethane polymer beads of appropriate hardness are obtained from a commercial source that specializes in this product. The polymer beads are obtained in two hardnesses H1 and H2. The H1 polymer beads (for example 55 Shore D) is harder than H2 polymer beads (for example 80 Shore A). An appropriate mass of H1 polymer beads is placed in the injection mold reservoir for the first polymer H1. An appropriate mass of H2 polymer beads is placed in the injection mold reservoir for the second polymer H2. The polymers are heated to appropriate injection temperature.

Using appropriate gate valves and pressure the polymers are injected into the mold. In one mold configuration the H2 polymer enters on the side that will be the articular cartilage surface and said H1 polymer enters on the side that will be the bone side of the plug. The two polymers meet and exit at the outflow port located at the desired level of the interface between the two polymers. A precise volume of said H1 polymer enters the plug mold from the bone side of the plug. During this injection, the gate control valve is activated to allow injection of a precise amount of said H2 polymer such that displacement of the H1 polymer by said H2 polymer forms an interface at the desired level on the plug. After injection molding is complete, the plugs are removed and flashing removed. The plugs are ultrasonically cleaned and rinsed and prepared for packaging and sterilization.

Similar methods may be employed to form laminates having three or more layers.

Method 3

In this method cylinders of two different polymer hardnesses H1 and H2 are obtained as described in method I and at least the H2 cylinder is complete with fixation barbs or ribs. The cylinders are placed in an alignmentjig that hold said cylinders in collets that also align said cylinders in axial alignment. The collets are mounted on linear rails that allow them to move the cylinder ends for joining. In practice the faces of cylinders H1 and H2 that are to be joined are slightly separated to allow the introduction of a nichrome or other appropriate heating wire element between the said cylinder faces. A voltage is applied to said heating wire allowing these surfaces to heat. At a critical fusion temperature, said heating element is removed and said collets are brought together allowing surfaces of said cylinders to fuse forming a laminate structure. The plug is allowed to cool and then removed from the collet assembly. Said plugs are ultrasonically cleaned and rinsed and prepared for packaging and sterilization.

Similar methods may be employed to form laminates having three or more layers.

Method 4

Extruded rods of biocompatible medical grade polyurethane polymer are available from a variety of commercial vendors specializing in this polymer as described in Method 1. Two rods of two different hardnesses, referred to as rod hardness 1 (H1) and rod hardness 2 (H2). For machining purposes, and because said rods of hardness H1 and H2 can be soft and pliable and may not cut when subjected to standard lathe machine turning techniques, the rods may be deep frozen to stiffen them for lathe turning and machining. Once the H1 rod is frozen, it is placed in a lathe chuck and the exposed end that is perpendicular to the long axis of the rod is faced and the diameter of the rod reduced to ½ the original diameter and threaded forming a threaded end (TEH1). A cylinder blank is then formed by cutting off the end portion of the said rod H1 at a predetermined length using a cutoff tool that allows secondary machining to obtain matching curves to the articular cartilage implantation target site.

The H2 rod is deep frozen and similarly chucked for turning but its surface parallel to the long axis is surface machined to form the desired ribs or barbs, after which the exposed end surface that is perpendicular to the long axis of the rod is faced off and center drilled. The end is then bored out and threaded to match the threaded end TEH1 of said H1 cylinder. A cylinder blank is then formed by cutting off the end portion of the said rod H2 at a predetermined length using a cutoff tool forming a flat bottom surface of the cylinder identified as surface SD.

The cylinders H1 and H2 are then cleaned and rinsed of any machining debris. The cylinders are then assembled by threading the end TEH1 of said cylinder H1 into the threaded hole located in the end of said cylinder H2. After inspection of the fit, the cylinders are disassembled and an appropriate aliquot of suitable glue is applied the base of the threaded hole and the cylinders quickly reassemble so that the glue may bond the threaded surfaces together forming a laminate structure. After the glue is cured, the finished plug is then ultrasonically cleaned and rinsed and prepared for packaging and sterilization.

Similar methods may be employed to form laminates having three or more layers.

A pore structure or surface asperity may imparted to a plug of the present invention using any of a number of techniques. For example, crystals or powders of suitable dimensions of non-toxic soluble compounds, for example, but not limited to sucrose, salt, calcium carbonate, sodium bicarbonate, etc. may be added to the mold process whereby they become imbedded in selected portions of the polymer.

Since these compounds are water soluble, they may be removed from the polymer by dissolving them in a water bath. Residual crystals not removed by the waterbath may eventually be naturally dissolved with no untoward effects as they are non-toxic. Different size crystals may be used in different portions of the plug and/or in different polymers to be combined to form the plug in order to provided differently sized pores in selected portions of the plug. For example, in a plug anchor application, it may be desirable to have smaller sized pores in that region of the plug that will be in direct contact with the subchondral bone in order to promote biologic fixation therewith, while the surfaces to be exposed to a flowable polymer will benefit from larger sized pores in order to facilitate the influx of the polymer and promote mechanical fixation therewith. Regardless of whether the plug has pores formed therein, it is desirable for all surfaces to be treated in a manner to provide conditions for cell attachment and biologic fixation. Such surface treatment may be accomplished by exposure to energetic plasmas, e.g. hydrogen peroxide plasma or argon plasma. An added benefit to such treatment is that the exposure aids in removal of minor contamination and also renders the surface sterile. Surface treatments may range from conservative techniques imparting subtle changes in asperity to the surface to aggressive techniques resulting in larger porosities.

The present invention also includes a process or procedure for resecting a portion of defective cartilage and filling the void cavity thereby created by implanting therein one or more cartilage replacement plugs according to the present invention. The present invention still further includes a set of operating instruments utilized in the procedure. Both the procedure and the instruments utilized in performing it will now be described.

According to the process, an orthopedic surgeon first ascertains the extent, shape and dimensions of the cartilage defect, resulting either from traumatic injury or chronic disease, by means of radiographic analysis or other standard diagnostic methods.

Figure 9A:
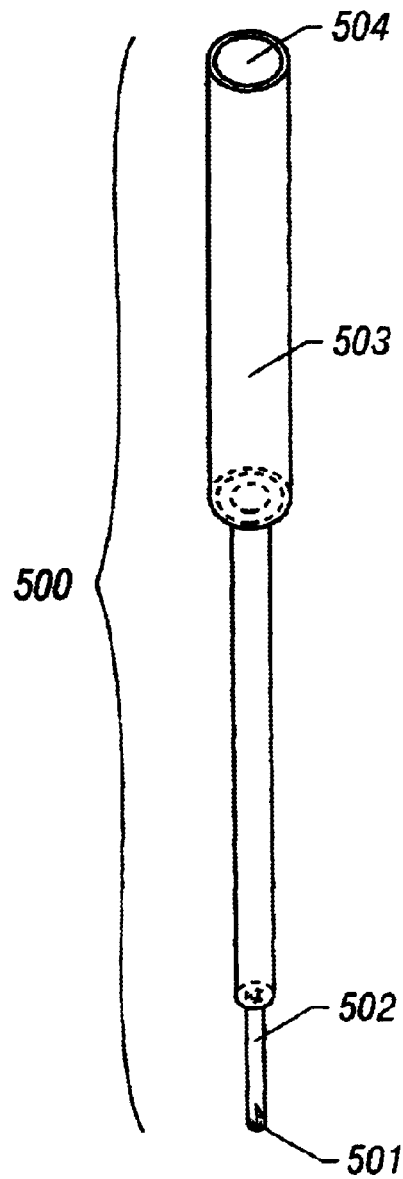

Referring to FIG. 9a, the general situs of the cartilage defect is surgically opened and an approximate center of the cartilage defect is marked and scored using cartilage scoring and pointer instrument 500. This instrument has a solid sharpened pointed tip 501 at a distal end 502 thereof for scoring the cartilage or just the outer layer of the cartilage at the location where the defect is to be removed. The instrument also has a handle 503 at a proximal end 504 of the instrument. The instrument may additionally include a hatched cutting surface with an outer core.

Figure 9B:
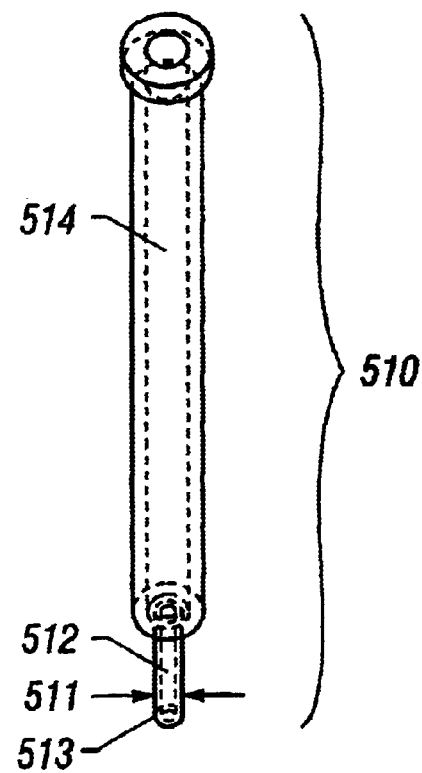

Referring to FIG. 9b, after marking the center of the defect that is to be resected, cartilage punch 510 is centrally positioned over the scored marking point on the outer surface of the cartilage and is used to punch an outline of the end view of the shape that is to be removed into the cartilage at the site of the defect. This in effect sets the perimeter of the defect that is to be removed. Cartilage punch 510 may have an adjustable punch diameter or width 511 whereby the diameter or width of the cartilage defect "core" which is to be resected can be set, or alternatively, a set of punches of fixed diameter or width can be utilized with a punch of appropriate size being selected for any given procedure. Cartilage punch 510 has a hollow tubular distal end section 512 with a sharpened edge or attached cartilage cutting blade 513 around the periphery of the tubular distal end section, such that the sharpened edge or blade is directed outwardly from the instrument and a proximal handle section 514. The hollow tubular distal end section 512 of cartilage punch 510 and the cartilage cutting blade 513 both have the same cross sectional shape and area. Generally, the cartilage punch 510 has a cross sectional shape corresponding to the shape of the cartilage replacement plug that is to be implanted. Typically, this will be a circular cross section, although any shape cross section may be utilized, including non-circular curvilinear shapes such as ovals, ellipses, and irregular closed curvilinear shapes, and polygonal shapes.

Figure 9C:
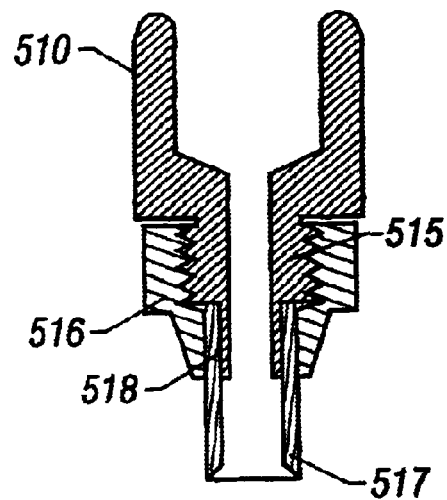

Referring to FIG. 9c, an alternative tip design for cartilage punch 510 shown in FIG. 9b allows for a disposable tubular punch section 517 to be used in scoring the articular cartilage repair site. Said disposable punch section 517 has a shoulder flange 518 that seats against the distal end 515 of punch 510 and is secured with a locking nut 516.

Figure 9D:
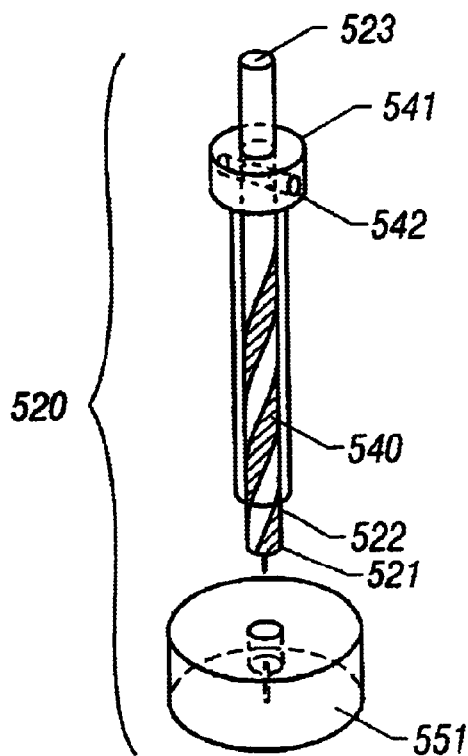

Referring to FIG. 9d, actual resection of the cartilage defect is next commenced using first drill instrument 520 to drill into the defective cartilage inside the previously designated perimeter. The action of the drill pulverizes the defective cartilage which is thereby removed leaving a void space for implantation of the cartilage replacement plug or plugs. First drill instrument 520 has a flat bottomed bit 521 at distal end 522 thereof which produces a drilled cavity in the cartilage having a generally cylindrical shape. First drill instrument has a handle 523 at a proximal end of the instrument.

Figure 9E:
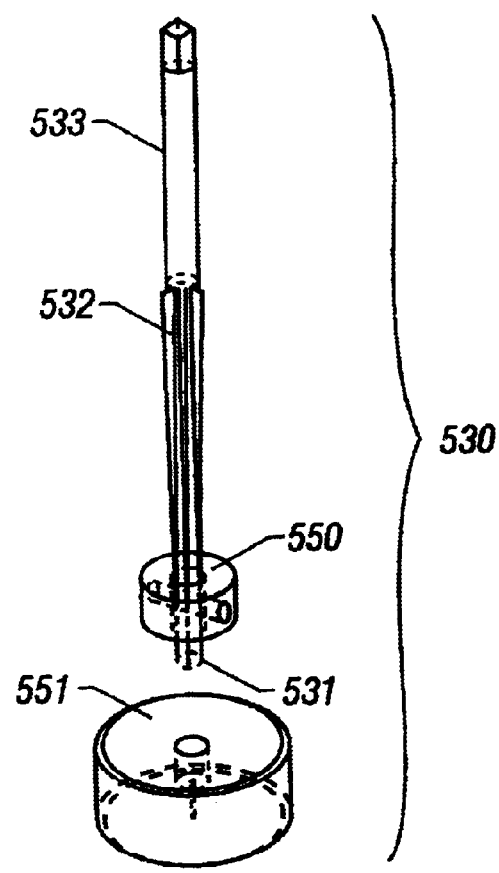
Figure 10:
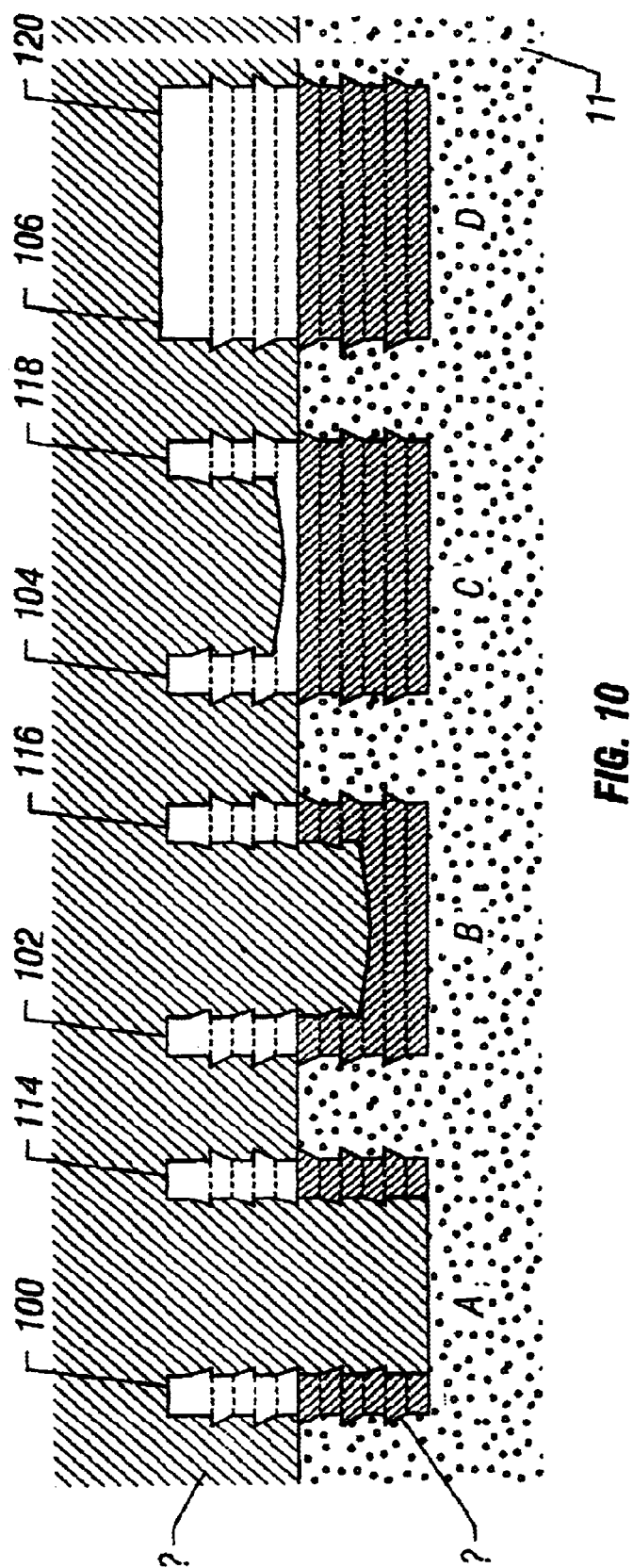
FIGS. 10a–d illustrate anchor plugs of the present invention in place within a repair site.

Referring to FIG. 9e, second drill instrument 530, having a tapered bit 531 at a distal end 532 thereof, is then used to produce a tapered distal end in the drilled cavity. Second drill instrument also has a handle 533 at a proximal end of the instrument.

Referring to FIG. 9d, depth gauge 540 may be utilized to control the depth of the cavity which is drilled by either the first drill instrument 520 or the second drill instrument 530. Depth gauge 540 is alternatively attachable to the first drill instrument 520 and the said second drill instrument 530 as they are used in sequence as described above to measure the depth of penetration into the cartilage of each of the first and second drill instruments, respectively.

Referring to FIG. 9e, drill stop 550, which is also is alternatively attachable to the first drill instrument 520 and the said second drill instrument 530, and which cooperates with the depth gauge 540, may be used to cause penetration of each of said first and second drill instruments into the cartilage to stop at a predetermined depth.

Referring to FIG. 9f, after the void cavity has been completely cleaned and prepared, cartilage plug insertion instrument 560 is then used to insert a preselected cartilage replacement plug, or, a series of plugs, sequentially, into the void cavity in the cartilage.

Referring to FIG. 9g, an alternate cartilage plug insertion instrument 570 with central drive 571 may be used to seat a plug into the void cavity in the cartilage.

EXAMPLE 1

A pilot study utilizing preformed polyurethane cartilage replacement plugs according to the present invention, fabricated in both hard and soft versions, and having both ribbed and barbed fixation elements, was undertaken for the repair of full thickness medial femoral condylar damage in the goat with the objectives of: determining the effectiveness of repairing a full thickness cartilage defect with a polyurethane plug; determining the ease with which such plugs can be fixed into a defect; determining the necessity of having a hard or a soft layer in contact with the opposing joint surface; determining the criticality of matching the surrounding surface contour; determining the extent to which the implanted cartilage replacement plug prevents further damage to surrounding cartilage; determining an appropriate tribological environment within a repaired joint by observing the hydrodynamic lubrication of compliant polyurethane bearing surfaces; and determining how well the implanted cartilage replacement plugs remained in place following function of the joint.

Under strict asepsis, a subchondral defect (40% by area) was created in the right medial femoral condyle of 4 adult, skeletally mature, disease-free, female Spanish goats. The cartilage defects created were 6 mm in diameter and 6 mm in depth, passing well into the subchondral bone. The defects were made 15 mm distal to the condyle groove junction and were aligned with the medial crest of the trochlear groove. The cartilage core cutter instrument according to the present invention was used first to slice through the cartilage layer to prevent tearing of the cartilage during drilling. With the core cutter in place, the centering awl instrument according to the present invention was introduced to locate the center of the core and allow for the point of the 6 mm drill bit to be located properly. A 6 mm collared drill bit was used under power to drill to a fixed depth of 6 mm, maintaining a drill plane perpendicular to the tangent of the condyle after which the drill bit was carefully removed. The appropriate cartilage plug implant was manually inserted and tapped into place with the insertion device instrument of the present invention. The joint was routinely closed. The opposite leg served as an unoperated control.

In all, two groups of two goats each were fitted with artificial cartilage plugs according to the present invention, made from hard and soft materials and using ribbed and barbed fixation means, as follows:

| Animal | Plug Material | Fixation Means |
|---|---|---|
| 1 | Hard | Ribbed |
| 2 | Hard | Barbed |
| 3 | Soft | Ribbed |
| 4 | Soft | Barbed |

Six weeks after the cartilage plug implantation surgery, all subject animals were humanely euthanized according to guidelines set forth by the AVMA Panel on Euthanasia. The operated and control joints were opened, grossly evaluated according to established criteria. The femora were cut approximately 10 cm above the joint line and split sagittally along the intercondylar notch. The control and implanted medial femoral condyles were fixed for histologic processing and analysis.

The results of the gross and histologic evaluation showed that fixation could successfully be achieved into the subchondral space with either barbs or ribs and that replacement of the defect with an artificial cartilage plug prevented further damage to the surrounding articular cartilage.

EXAMPLE 2

The cartilage plugs of the present invention may alternatively be used to anchor a flowable polymer to the subchondral bone. An implantation hole for the plug is drilled into the prepared bony base of the articular cartilage defect. Preparation of the bony base of the defect in this context entails the removal of loose tissue debris and exposure and/or surface modification of part or 11 of the subchondral bone in the defect area by the surgeon. Using an inserter instrument that holds and drives the plug for implantantion, the base unit is inserted into the bone to a depth of approximately 50–60% of the plug height. The cylindrical devices are seated such that approximately half of the barbs or ridges on the outer surface of the plug engage the bony walls of the tunnel and the remaining half of the plug's external ridges remain exposed. The inserter tool is removed and rearmed with another anchor plug as necessary and the process is repeated. Multiple anchor plugs may be placed in a variety of patterns at the base of the lesion site as desired by the surgeon.

Once the anchor plugs are in place, a flowable polymer is introduced into the defect site. The flowable polymer will flow into the lesion site, including in and around the implanted plugs as well as into any bores that may be formed in such plugs. At an appropriate fill level, the flowable polymer will cover the anchor plugs with an overlay of polymer approximately 3 mm above the top the plugs or to an overlay determined to be appropriate from surgeon experience. The flowable polymer is allowed to polymerize and cure. The action of the curing process of the flowable polymer to the interior and exterior surfaces of the plug will provide for a mechanical fixing of the flowable polymer to the subchondral bone. Any ridges in the form of ribs or barbs in parallel or helical arrangements, on the exterior and interior surfaces will further enhance the mechanical fixation. Any adhesive qualities of the flowable polymer will also help to augment the desired fixation to the anchor plug. In addition, such polymerization will result in a multi-laminate structure in conjunction with the plug device. Transmission of load to subchondral bone will be through the flowable polymer and polymer plug anchor device interface. Load transmission is believed to be beneficial to biologic fixation of the anchor device and in turn the fixation of the flowable polymer in the correct anatomic location.

FIGS. 10a–d illustrate four different plug configurations implanted in subchondral bone. Each anchor plug 100, 102, 104, 106 is formed of two different polymers 108, 110 wherein the harder polymer comprises that portion of the plug in contact with the subchondral bone 112 while the softer polymer comprises that portion of the plug that extends above the surface of the bone. All of the plug embodiments that are illustrated have barbs formed on their external surfaces. Plug 100 has a bore 114 formed therein that extends through its entire length, while plugs 102 and 104 have bores 116, 118 formed therein that only extend partially into the plug. All of the plugs with bores have barbs formed in the their interior surfaces. The barbs formed on the exterior of the plugs are oriented so as to resist pull-out of the plug from the bone while the barbs formed on the interior are oriented to resist the pull-out of cured polymer 120 from therewithin. After the implantation of the plugs into the subchondral bone, a flowable polymer is poured thereover which completely encapsulates the plugs, intrudes into the bores and covers the plugs to a predetermined depth. The polymer adheres to the plugs and the subcondral bone and additionally becomes mechanically fixed to the plugs to form an additional layer in the laminate structure.

Figure 11B:
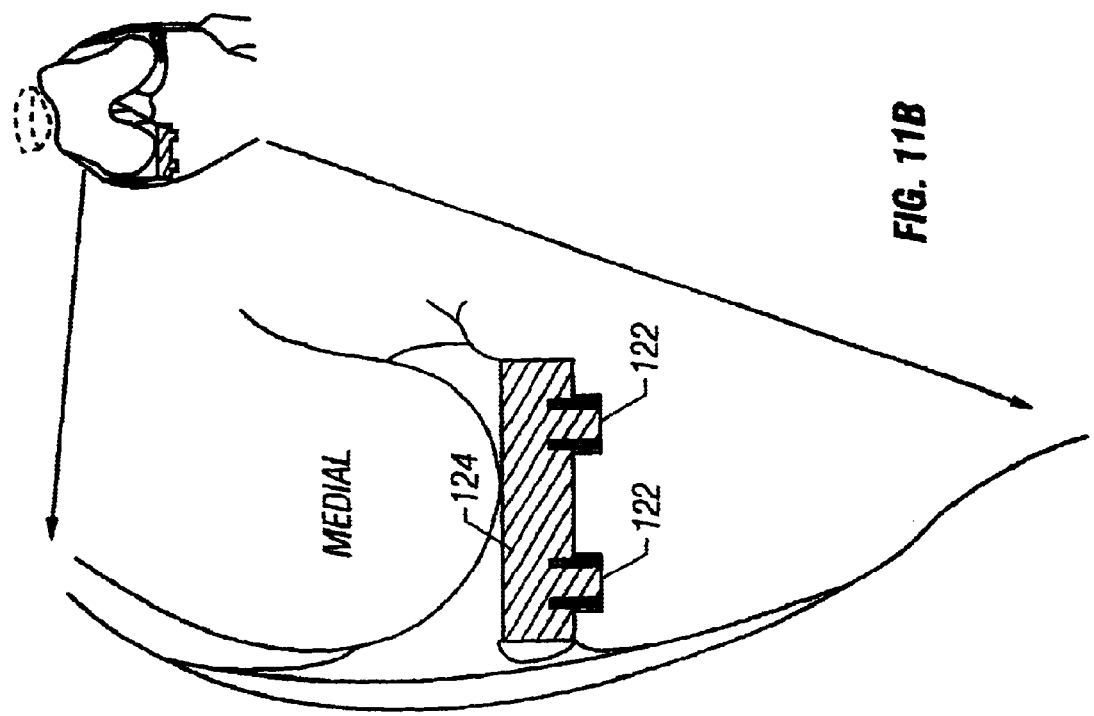
FIGS. 11a and b schematically illustrate a surgical site in which anchor plugs of the present invention are employed.
Figure 11A:
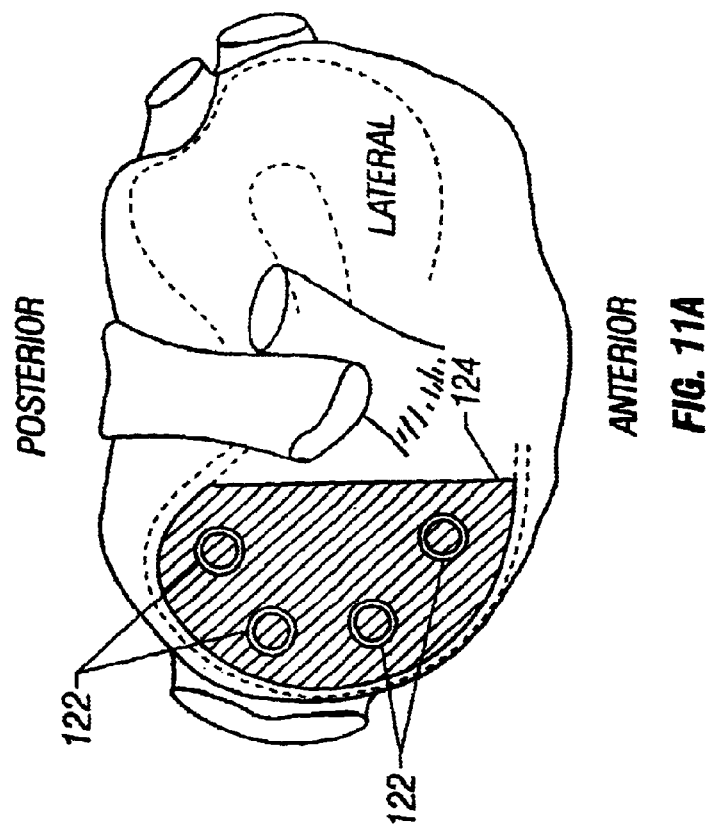

FIG. 11 schematically illustrates an example of a surgical site wherein four artificial cartilage plugs 122 serve to anchor a flowable polymer 124 in place. The knee repaired in such manner will have the cured polymer mechanically and adhesively fixed in place. The plug anchors are in turn mechanically fixed in the bone and will eventually additionally become biologically fixed thereto.

While particular forms of the invention have been illustrated and described, it will also be apparent to those skilled in the art that various modifications can be made without departing from the spirit and scope of the invention. Accordingly, it is not intended for the invention to be limited except by the appended claims.

What is claimed is:

1. A cartilage plug for insertion into a void in a cartilaginous tissue in a living mammal, comprising:

a substantially rigid laminated preformed mass of artificial biocompatible and exclusively polymeric materials wherein said materials are arranged in layers, each material having different mechanical, physical properties, and hardnesses; and wherein said void extends to subchondral bone and wherein said plug is configured so as to be received in such void such that a second end of said plug contacts said bone, wherein said second end is formed of a material having an elastic modulus similar to subchondral bone; and wherein said plug is configured so as to be received in said void such that a first end becomes aligned with the surface of surrounding cartilaginous tissue, where such first end is formed of the least hard of said materials.

* * * * *